United States Patent [19]

Chujo

[11] Patent Number: 4,990,235
[45] Date of Patent: Feb. 5, 1991

[54] OXYGEN SENSOR

[75] Inventor: Yoshiki Chujo, Mishima, Japan

[73] Assignee: Toyota Jidosha Kabushiki, Toyota, Japan

[21] Appl. No.: 477,734

[22] Filed: Feb. 9, 1990

[30] Foreign Application Priority Data

Feb. 23, 1989 [JP] Japan .................. 1-019507[U]
Feb. 27, 1989 [JP] Japan .................. 1-043167

[51] Int. Cl.$^5$ .................................. G01N 27/407
[52] U.S. Cl. .................... 204/424; 204/153.18; 204/425; 204/426; 204/427; 204/429
[58] Field of Search ............... 204/153.18, 421–429

[56] References Cited

U.S. PATENT DOCUMENTS

| 4,158,166 | 6/1979 | Isenberg | 204/426 |
| 4,272,329 | 6/1981 | Hetric et al. | 204/1 |
| 4,496,455 | 1/1985 | Linder et al. | 204/425 |
| 4,505,806 | 3/1985 | Yamada | 204/452 |
| 4,574,627 | 3/1986 | Sakurai et al. | 204/426 |
| 4,728,411 | 3/1988 | Mase et al. | 204/426 |
| 4,776,943 | 10/1988 | Kitahara | 204/425 |
| 4,875,990 | 10/1989 | Kodachi et al. | 204/425 |
| 4,905,654 | 3/1990 | Katsuno et al. | 123/494 |

FOREIGN PATENT DOCUMENTS

56-130649 10/1981 Japan.

Primary Examiner—T. Tung
Attorney, Agent, or Firm—Kenyon & Kenyon

[57] ABSTRACT

An oxygen sensor having a body formed of a solid electrolyte material on which electrodes are provided, and a diffusion chamber formed on one side of the body. The diffusion chamber is connected to the space in which the gas to be detected exists, i.e., the interior of the intake or exhaust pipe of an internal combustion engine. A plate is mounted on the body in which a pin-hole is formed for controlling the speed of diffusion of oxygen ions so that the concentration of oxygen ions in the diffusion chamber is equal to that in the detection space. A pore of pores is provided in a plate member forming the diffusion chamber, to enable a rapid equalization of the pressures of the detection space and diffusion chamber while maintaining a control of the diffusion of oxygen ions via the pin-hole.

9 Claims, 7 Drawing Sheets

OXYGEN SENSOR

BACKGROUND OF THE INVENTION

1. Field of the Invention

The present invention relates to a limit electric current type oxygen sensor capable of detecting a density of oxygen in an internal combustion engine.

2. Description of the Related Art

The most popular type of oxygen sensor is an oxygen density cell having a body formed of a solid electrolyte material such as zirconia. In this type of oxygen sensor, an electromotive force is generated when the air-fuel ratio of the gas to be detected is higher than a predetermined air-fuel ratio value corresponding to a chemical stoichiometric value, i.e., a theoretical air-fuel ratio, and therefore, this type of sensor can only discriminate whether or not an electromotive force has been generated, i.e., the sensed air-fuel ratio is lower or higher than the theoretical air-fuel ratio.

Accordingly, a limit electric current type oxygen sensor has been proposed whereby a detection of the wide range of values of the air-fuel ratio between the lean side and the rich side of the air-fuel ratio is possible. This limit electric current type oxygen sensor usually comprises a body formed of a solid electrolyte material, a perforated oxygen diffusion speed control layer formed on the solid electrolyte body and an electrode arranged on the solid electrolyte body in such a manner that it is covered by the diffusion speed control layer. In this type of sensor, when an electric voltage is applied to the electrode, an electric current is generated in the solid electrolyte body, and the generated electric current basically varies in accordance with the electric voltage applied when the oxygen density remains at a predetermined value. However, a range of values of the electric voltage applied to the electrode exists at which the value of the electric current is unchanged (or is saturated) due to the provision of a diffusion speed limit area for controlling the speed of the diffusion of oxygen ions via the perforations in the oxygen diffusion speed control layer. This value of the electric current in the saturated zone, called the limit electric current, has a predetermined proportional relationship to the oxygen density, and therefore, in a known device an electric current (i.e., pumping electric current) applied to the sensor is controlled to maintain the voltage applied to the electrodes at a predetermined value, so that the saturating electric current corresponds to the oxygen density. Namely, the value of the oxygen density can be determined from the value of the detected electric current.

In this type of oxygen sensor, wherein the diffusion velocity control layer is formed of a perforated material, the diffusion velocity is greatly dependent on the temperature of the sensor, and therefore, a temperature compensation circuit must be included for compensating the effect of the temperature on the detected value of the oxygen density, which requires a complicated construction of the sensor.

In view of the above, a limit electric current type oxygen sensor was proposed in which a pin-hole is employed as the diffusion speed control means (see Japanese Un-Examined Pat. Publication No. 56-130649). In this pin-hole type sensor, a diffusion chamber is formed on one side of the solid electrolyte body and is connected, via the pin-hole, to an area in which the gas to be detected is located. The pin-hole controls the speed of the diffusion of oxygen ions such that the oxygen density of the gas in the area on one side of the pin-hole is the same as the oxygen density on the other side of the pin-hole, i.e., in the diffusion chamber. The diffusion via the pin-hole is a particle diffusion process, which has a much smaller temperature dependency with regard to the diffusion speed than the diffusion carried out via the conventional perforation under the Knudsen diffusion principle. Therefore, the pin-hole type sensor has an advantage in that a relatively simple circuit can be used to compensate the temperature dependency, to thereby detect a precise value of the air-fuel ratio.

In this pin-hole type diffusion oxygen sensor, the diffusion velocity depends greatly on the pressure parameter. Namely, the precision of the value of the oxygen density as detected is influenced by a pressure pulsation, for example, in the intake passageway of an internal combustion engine, i.e., the oxygen particles are introduced into or discharged from the diffusion chamber, via the pin-hole, in accordance with an increase or decrease generated by the pulsation of the intake pressure. Nevertheless, the speed of introduction of the oxygen particles and the speed of exhaust of the oxygen particles are not the same, i.e., the speed of introduction of the oxygen particles into the chamber due to the increase in the pressure is higher than the speed of the exhausting of the oxygen particles from the chamber. Accordingly, to evenly balance the introduction of the oxygen into the chamber and the exhaust of the oxygen from the chamber, the amount introduced must be larger than the amount exhausted, and therefore, a larger electric current is obtained than would be if a pressure pulsation did not occur, even when the oxygen density is unchanged.

SUMMARY OF THE INVENTION

An object of the present invention is to provide a pin-hole diffusion principle type oxygen sensor capable of eliminating an effect on the precision of detection of the oxygen density due to pulsations of the intake pressure.

According to the present invention, an oxygen sensor is provided for detecting the oxygen density of a gas in an area to be detected, the sensor comprising a body formed of a solid electrolyte material; a diffusion chamber formed on one side of the solid electrolyte body; a means for controlling the speed of the diffusion of oxygen ions between the detecting area and the diffusion chamber; an electrode means mounted on the electrolyte body as a sensor cell for generating an electric voltage across the body, and a pumping cell for controlling a value of the electric current thereof. The diffusion speed control means comprises at least one pin-hole for connecting the gas to be detected to the diffusion chamber, and a perforation means for connecting the gas to be detected to the gas in the chamber, to enable a rapid equalizing of the pressures in the detecting area and the diffusion chamber while maintaining the rate of diffusion of oxygen particles via the pin-hole.

DESCRIPTION OF THE PREFERRED EMBODIMENTS

Figure 1:
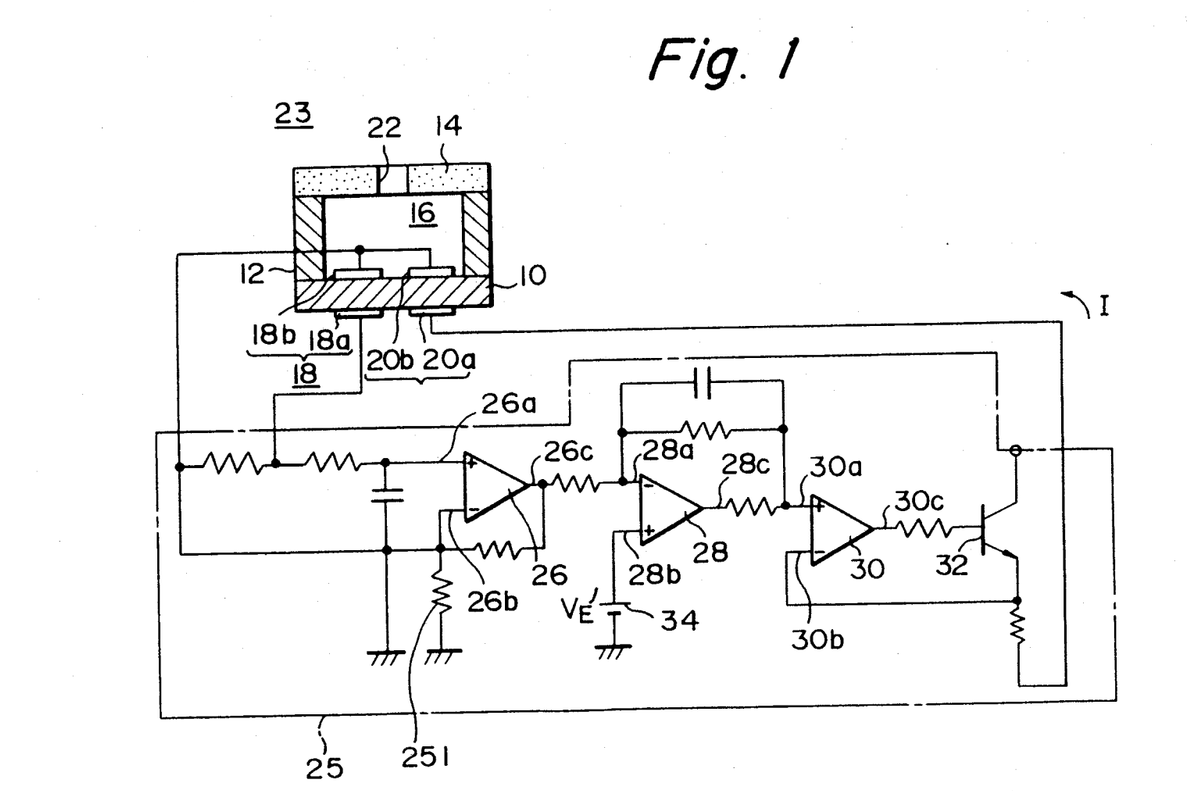
FIG. 1 shows an embodiment of an oxygen sensor and the control circuit therefor.

FIG. 1 shows a first embodiment of an oxygen sensor, according to the present invention, arranged in an intake passageway of an internal combustion engine. The sensor is provided with a body 10 formed of a solid state electrolyte material, such as a stabilized zirconia, on which an orifice plate 14 is fixedly mounted via a tubular-shaped spacer 12, and a diffusion chamber 16 is thus formed between the body 10, spacer 12, and orifice plate 14. The sensor of this embodiment is provided with two pairs of electrodes 18a and 18b, and 20a and 20b, arranged on facing surfaces of the solid state electrolyte material body 10. As will be fully explained later, the set 18 of the electrodes 18a and 18b forms a sensor cell, and the set 20 of the electrodes 20a and 20b forms a pump cell. The orifice plate 14 has a pin-hole 22 formed at the center thereof. As will be fully described later, the orifice plate 14 is formed of sintered alumina and has a porous structure. The pin-hole 22 communicates the diffusion chamber 16 with a space 23 in an intake pipe of an internal combustion engine, in which the gas to be detected is located, and generates a diffusion of gas under the diffusion principle, permitting the oxygen density to be detected from a limiting electric current created in the pumping cell 20. In the diffusion mechanism occurring under the molecular diffusion principle, the control of the speed of diffusion of the oxygen molecules as diffused is carried out by causing a mutual collision of the oxygen molecules passing through the pin-hole 22. To obtain this type of diffusion speed control, the diameter of the pin-hole 22 is preferably between 0.1 mm to 0.8 mm. Note, another type of diffusion principle, referred to as a Knudsen type diffusion, is known wherein the diffusion is carried out across a porous material having very fine holes, each having a diameter of between 500 Å and 1500 Å. In this latter type of diffusion, the molecules of the oxygen diffuse while in repeated contact with the inner surfaces of the fine holes. As will be easily understood, the mechanisms for obtaining the diffusion of oxygen molecules by the above two diffusion principles are very different.

The principle of the detection of the oxygen density by the pin-hole type diffusion mechanism will be described hereinbelow.

The output voltage $V_E$ of the sensor cell 18 is found by the following equation:

$$V_E = (1/K) \times ln(PO_{2I}/PO_{2C}) \quad (1)$$

where, $PO_{2I}$: oxygen partial pressure in the gas in the intake system 23 of the engine $PO_{2C}$: oxygen partial pressure in the diffusion chamber 16

$K = 4 \times F/(R \times T)$

F: Faraday constant

R: Gas constant, and

T: Temperature of the element.

From the equation (1) the following equation is obtained by taking into consideration the pressure of the gas:

$$V_E = (1/K) \times ln(PO_{2I}/P_I)(PO_{2C}/P_C) \quad (2)$$

where, $P_I$ is a total gas pressure in the intake pipe 23, and $P_C$ is total gas pressure in the diffusion chamber 16. The limiting electric current passed through the pumping cell 20 is determined by the amount of $O_2$ subjected to the speed control operation by the pin-hole under Fick's law, and is calculated by the following equation:

$$I_P = K \times D \times (S/l) \times (PO_{2I} - PO_{2C}) \quad (3)$$

where, D is a diffusion coefficient of the oxygen $O_2$, S is the diameter of the pin-hole, and l is the length of the pin-hole. Then, from equations (1) and (3), the following equation is obtained:

$$PO_{2C} = PO_{2I} \times exp(-K \times V_E) \quad (4)$$

and from equations (4) and (3), the following equation is obtained.

$$I_P = K \times D \times (S/l) \times PO_{2I} \times (1 - exp(-K \times V_E)) \quad (5)$$

Here, K is inversely proportional to the temperature T, and the diffusion coefficient D is inversely proportional to the total pressure $P_I$. Therefore, if constant values of the temperature T and the electric voltage $V_E$ as generated are maintained, the following equation is obtained.

$$I_P = PO_{2I}/P_I \quad (6)$$

Figure 2:
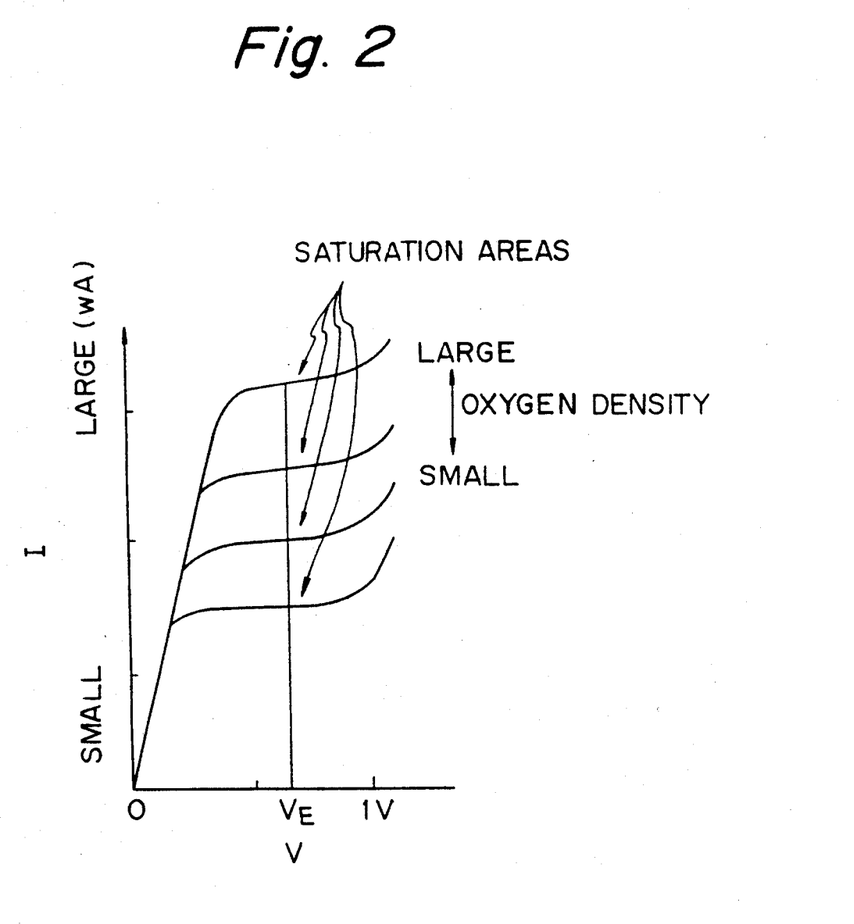
FIG. 2 shows the relationships between the voltage and the electric current with respect to various oxygen density values.
Figure 3:
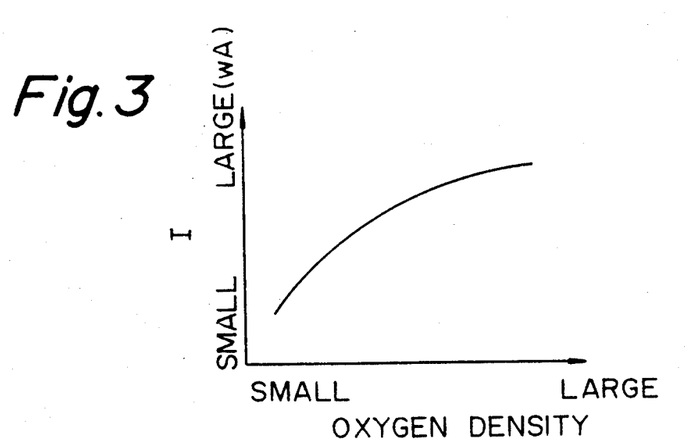
FIG. 3 shows the relationship between the oxygen density and the electric current.

Therefore, as shown above, it is possible for the degree of the limiting electric current to be determined only by the ratio of the oxygen partial pressure to the total pressure, i.e., the oxygen density. FIG. 2 shows the relationships between the voltage V and the electric current I with respect to various values of the oxygen density. As is clear from the curves shown in the figure, at each of the oxygen density values an electric voltage V area exists wherein the value of the electric current is saturated. This saturated value of the electric current is called the limiting electric current, and has a unique relationship with respect to the values of the oxygen density, as shown in FIG. 3. This means that it is possible to detect the oxygen density from the value of the electric current, if the voltage V is maintained at $V_E$, in the saturation areas for each of the oxygen density values. Furthermore, as described with reference to equation (6), this detection of the oxygen density provides a desirable characteristic in that it is not dependent on the value of the intake pressure.

Figure 4:
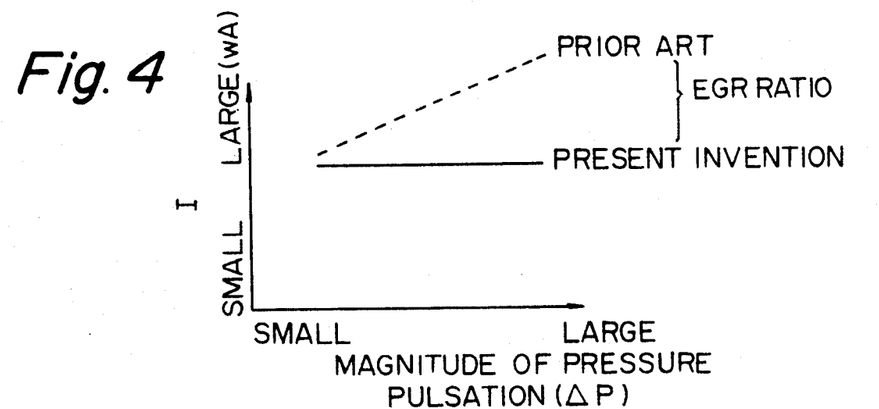
FIG. 4 shows the relationships between the magnitude of the pressure difference and the electric current.
Figure 5:
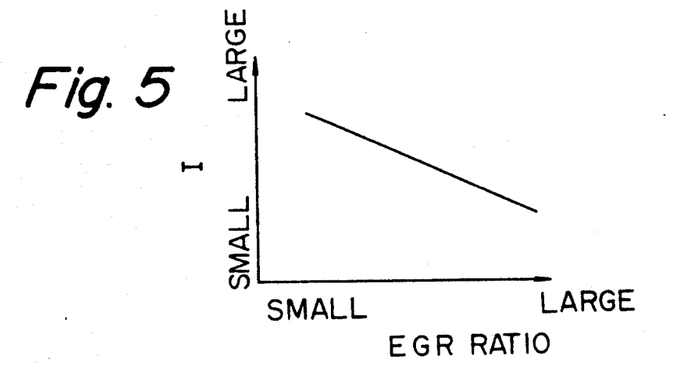
FIG. 5 shows the relationship between the air fuel ratio and the electric current.

Nevertheless, when the above type of sensor is actually arranged in the intake pipe of an internal combustion engine, the output level of the sensor is changed in accordance with the dynamic pressure in the intake pipe, due to the pulsations of the pressure in the intake pipe, and thus the precision of the detection of the oxygen density is lost, for the following reason. Note, there is an upper limit of the value of the diameter of the pin-hole 22 when employing the pin-hole diffusion principle, and due to this upper limit of the inner diameter of the pin-hole, the pressure in the diffusion chamber cannot be immediately made the same as the pressure in the intake pipe when pressure pulsations occur in the intake line. For example, assuming that a pulsative change in the intake pressure $P_I$ in the equation (2) has occurred, then in this case, a corresponding and immediate change in the pressure of the diffusion chamber 16 does not occur, and thus a temporarily unbalanced state exists between the oxygen density in the intake pipe, $PO_{2I}/P_I$, and the oxygen density in the diffusion chamber 16, $PO_{2C}/P_C$. As a result, the oxygen density as detected by the sensor is not the actual oxygen density in the intake pipe. Namely, the pin-hole type oxygen sensor suffers from a drawback of an inferior response speed characteristic, due to a slow transmission of the pressure in the intake pipe to the diffusion chamber 16. From the results of experiments carried out by the inventor, it was found that, during the change of the density of the oxygen $O_2$ in the intake pipe from 20% of the total pressure to 16% of the total pressure, it took from 0.1 to 0.2 seconds for the corresponding change in the output electric current in the sensor to be completed. A dotted line in FIG. 4 shows the relationship between the magnitude of the pulsation of the intake pressure, $\Delta P$, and the output electric current I, in the prior art. The dependence of the output electric current with respect to the pressure pulsation causes an incorrection detection of the oxygen density, and where the engine is provided with an EGR system, a correct detection of the EGR ratio (a ratio of the exhaust gas recirculated into the intake line from the exhaust line to the total amount of the gas, i.e., intake air and exhaust gas, introduced into the engine) is impossible.

According to the present invention, means are provided for defining perforations for rapidly balancing the pressure in the diffusion chamber with the pressure of the gas to be detected, while employing the pin-hole type diffusion principle. According to the present invention, a means is provided for cancelling an error in the detection of the oxygen density caused by the pulsation of the intake pressure. In the embodiment shown in FIG. 1, the orifice plate 14 is formed from a porous body of sintered alumina. The sintered alumina orifice plate 14 is provided with a plurality of fine pores having a diameter much smaller than that of the pin-hole 22, for example, about 1000 Å. It should be noted that the diameter of the each of the fine pores in the orifice plate is very small, and the diameters of all of the fine pores are such that the total area of the pores is 0.01% of the area of the pin-hole 22, which allows the pin-hole type diffusion to be employed and the pulsative change of the pressure in the intake passageway to be quickly transmitted to the diffusion chamber 16. Further, due to the provision of the fine pores having the dimensions mentioned above, it is possible to decrease the transmission time of the pressure from 0.1–0.2 seconds to 10–30 milliseconds, and accordingly, the pressure in the diffusion chamber 16 can be rapidly changed in accordance with the pulsative change in the pressure in the intake pipe 23, whereby an error caused by such a pulsative change is avoided. As can be seen from the solid line in FIG. 4, showing the relationship between the magnitude, $\Delta P$, of the pulsative pressure and the sensed electric current I, the dependence on the magnitude $\Delta P$ of the pulsation of the intake pressure sensor can be eliminated, and thus a precise detection of the EGR ratio can be made from the value of the electric current in the sensor.

In FIG. 1, a control circuit 25 is provided for controlling the electromotive force of the sensor cell 18 and the pumping current in the pumping cell 20. The control circuit 25 is per se known, and is comprised of operating amplifiers 26, 28, and 30, and a transistor 32. The first operating amplifier 26 amplifies the electromotive force generated by the sensor cell 18 and has a noninverted input 26a connected to the first electrode 18a of the sensor cell 18 and an inverted end 26b connected to the ground via a resistor 251. The second electrode of the sensor cell 18 is grounded. The second operating amplifier 28 serves as a comparator and has a first input 28a connected to an output 26c of the first operating amplifier 26 and a second input connected to a device 34 for setting a voltage $V_E$, corresponding to the voltage $V_E$ in FIG. 2. The third operating amplifier 30 has a first input 30a connected to the output 28c of the second operating amplifier 28 and a second 30b output connected to the emitter of the transistor 32, and has an output 30c connected to the base of the transistor 32. The emitter of the transistor 32 is connected to the first electrode 20a of the pumping cell 20, and the second electrode 20b of the pumping cell is connected to the ground.

The operation of the control circuit 25 will be described as follows. When the voltage level at the input of the operating amplifier 28 is higher than the predetermined voltage $V_E'$, the first operating amplifier 26 outputs a low level signal, and as a result, the input level at the input 30a becomes lower than the input level at the input 30b, whereby the second operating circuit 30 outputs a high level signal, making the transistor 32 OFF and decreasing the electric current in the pumping cell 20. As the electric current in the pumping cell is decreased, the output voltage of the sensor cell 18 is also decreased, and thus the input level at the input 28a becomes lower than the input level at the input 28b, and the comparator 28 outputs a high level signal. Accordingly, the level at the input 30a is higher than the level at the input 30b, and thus the transistor 32 is made ON. As is clear from the above, the control circuit 25 controls a predetermined voltage $V_E$ applied to the sensor cell 18, which is located in the zones for obtaining the limiting electric current for each value of the oxygen density, and thus it is possible to detect the value of the oxygen density from the value of the electric current I in the pumping cell 20.

Figure 6:
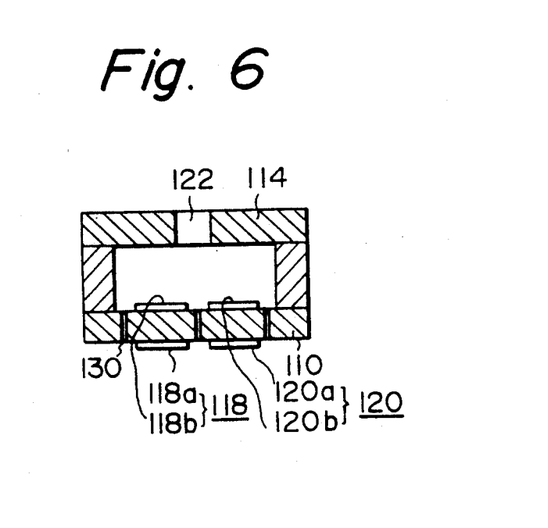
FIGS. 6 and 7, respectively, show other embodiments of the oxygen sensor according to the present invention.

FIG. 6 shows a modification of the oxygen sensor of the present invention, wherein the orifice plate 114 is a usual type formed from solid alumina material, and the main body 110 is provided with a plurality of pores 130. The dimension and number of the pores 130 are large enough to obtain a rapid transmission of the pressure and small enough to maintain the pin-hole type diffusion by the diffusion hole 122. The sensor cell 118 and pumping cell 120 are formed by electrodes 118a and 118b, and 120a and 120b, respectively. Each of the pores 130 has a diameter smaller than that of the pin-hole 122, but is much larger than the diameter of one inner hole in the porous plate 14 of the first embodiment. Furthermore, the diameters of the pores 130 and the total number thereof are determined such that the total area occupied by the pores 130 is 0.01% of the area of the pin-hole 122.

Figure 7:
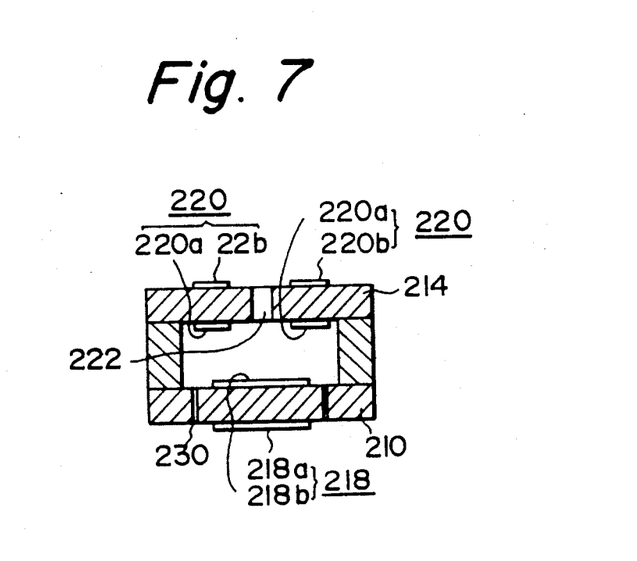

In the embodiment shown in FIG. 7, pressure balancing holes 230 are formed in the body 210 as in the embodiment of FIG. 6, the electrodes 218a and 218b forming the sensor cell 218 are formed in the body 210, and the electrodes 220a and 220b forming the pumping cell 220 are formed in the orifice plate 214.

Figure 8:
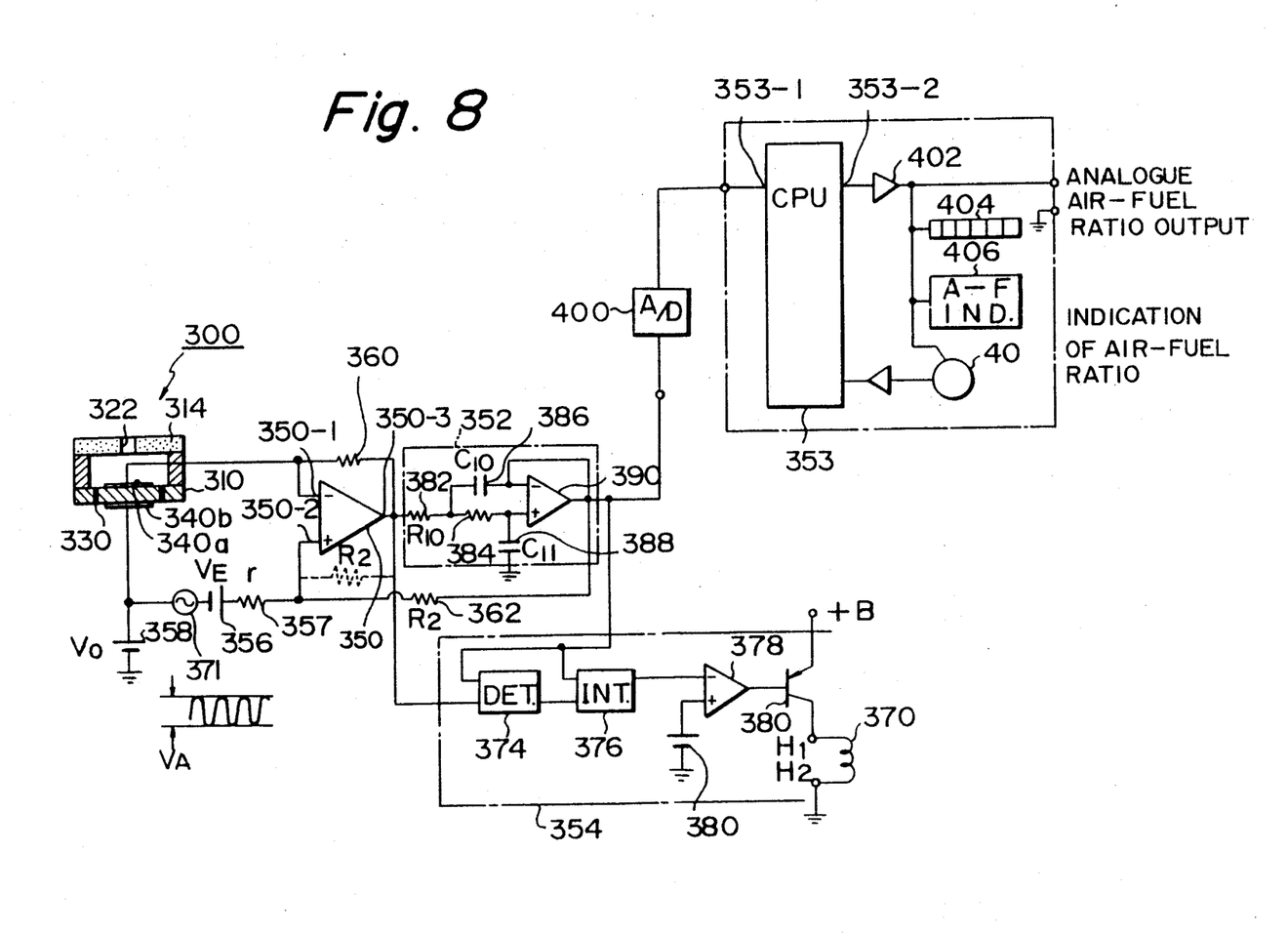
FIG. 8 shows another embodiment of the oxygen sensor, as an air-fuel ratio sensor, and the control circuit therefor.

In the embodiment illustrated in FIG. 8, a sensor is provided with a means for obtaining a rapid balancing of the pressures, and similar to the embodiment of FIG. 1, is formed by porous plate 314 formed from a porous material and a base plate 310 defining a plurality of pressure balancing holes 330. The feature of this embodiment is that only electrodes 340a and 340b form the sensor cell and pumping cell. Note, a sensor wherein a pair of electrodes can operate not only as a sensor cell but also as a pumping cell is per se known, but in this embodiment, a control circuit for processing signals from the sensor to detect the oxygen density is provided. This control circuit includes a first operating amplifier 350, a low-pass filter unit 352 connecting the oxygen sensor signal control unit to a microcomputer unit 353, for controlling the operation of the air-fuel ratio control operation of an internal combustion engine, and a heater control unit 354 for controlling the operation of a heater of the oxygen sensor; these units 352 and 354 will be fully described later.

The operating amplifier 350 generates an electric current corresponding to the pumping electric current while maintaining the electric voltage applied to the electrodes 340a and 340b at a constant value. Namely, the operating amplifier 350 corresponds to the control circuit 25 of FIG. 1. The operating circuit 350 has a first inverted input 350-1, a second non-inverted input 350-2, and an output 350-3. The first input 350-1 is connected to the first electrode 340a, and the second input 350-2 is connected to an end of the electric voltage source 356 via a resistor 357. The other end of the electronic source 356 is connected, together with the second electric voltage source 358 $V_0$, to the ground. The output 350-3 of the operating amplifier 350 is connected to the inverted input 350-1 thereof via a first feed back resistor 360 having a value R1, and a second feed back resistor 362 having a value R2 connects the output of the low-pass filter 352 to the non-inverted input 350-2 of the operating amplifier 350.

The first feed back resistor 360 carries out an electric current corresponding to the pumping current in the sensor, i.e., the oxygen density, and the resistor 357, which is in series with the electric voltage generator 356, controls the voltage level at the second input 350-2 of the operating amplifier 350.

Figure 9:
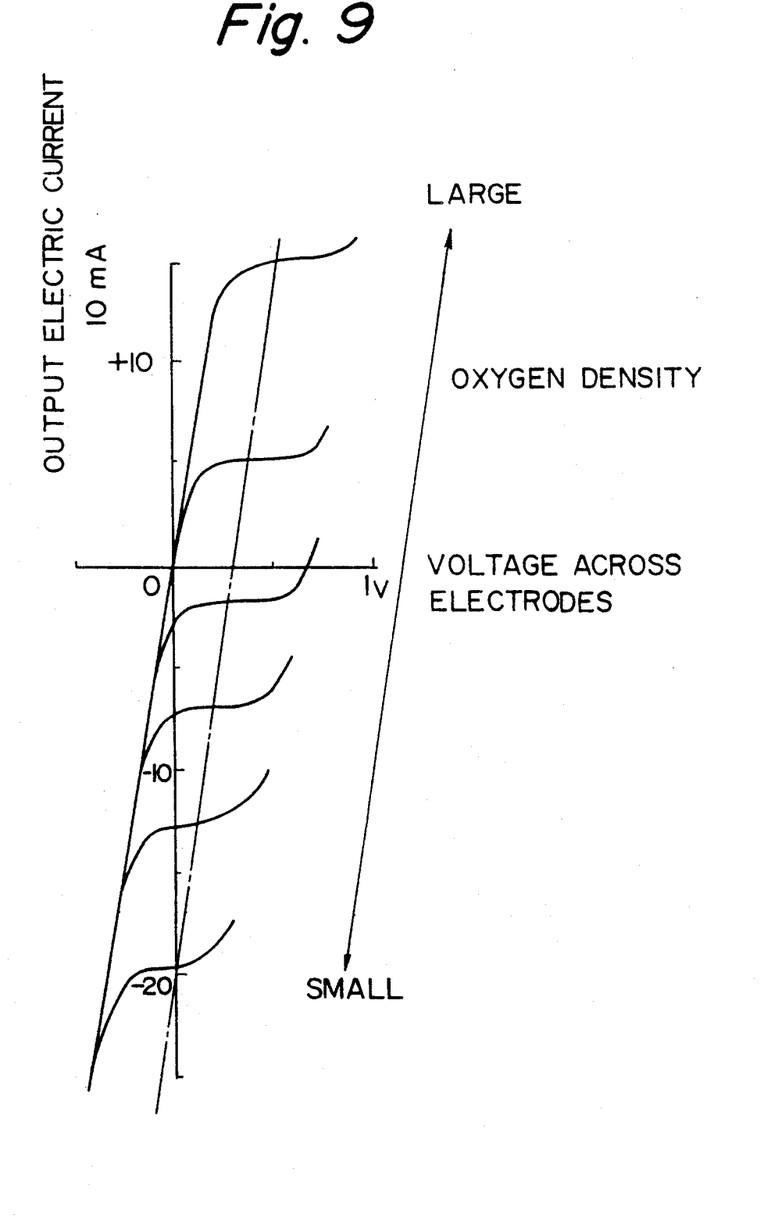
FIG. 9 shows the relationships between the voltage and the electric current with respect to various air-fuel ratio values; and, FIG. 10 shows the relationships between the air-fuel ratio and the sensor output level before and after correction, respectively.

FIG. 9 shows the relationship between the electric voltage and the electric current in this type embodiment of the sensor. As can be seen from FIG. 9, the range at which a saturated electric current is obtained is shifted toward the high voltage side as the density of the oxygen becomes greater. This shift is caused by an internal resistance of the sensor, which allows the sensor to generate an electromotive force equal to the electric current multiplied by the value of the internal resistance. The control circuit in FIG. 8 can detect the limiting electric current regardless of the influence of the internal resistance of the sensor. To accomplish this, the operating amplifier 350 basically operates to maintain a constant electric voltage across the electrodes 14a and 14b which is equal to the voltage level $V_E$ generated by the generator 356. Furthermore, the second feed back resistor 362, which carries an electric current proportional to the pumping electric current is connected in series to the resistor 357, which is connected in series to the generator 356. As a result, a voltage drop generated in the resistor 357 is proportional to the pumping current, and thus the voltage level at the input 350-2 of the operating amplifier 350 is changed in accordance with the change of the value of the pumping current. The value of the resistor 357 can be suitably selected so that the value of a voltage applied across electrodes 340a and 340b is controlled as shown by the dotted line in FIG. 9, whereby the electric current (limiting current) at the saturating zone can be detected over the entire range of the density of the oxygen to be detected. It should be noted that, from the point of view of the equivalent circuit, the electric voltage sources 356 corresponds to the electromotive force and the resistor 357 to the internal resistance of the sensor. It should be also noted that the second electric voltage source 358 is used to offset the sensor output current characteristic to the positive side, i.e., to displace it so that the output current from the sensor always has a positive value.

The sensor of the embodiment in FIG. 8 is also provided with a circuit for compensating the temperature of the sensor. The output characteristic of this type of sensor has only a limited dependency on the temperature, but preferably the temperature compensation system is provided to increase the precision of the detection of the oxygen density. Furthermore, the sensor is directed to the detection of the air-fuel ratio of the air-fuel mixture introduced into an internal combustion engine, and therefore, since the heater 370 is provided for heating the sensor element 330, the temperature compensating circuit is also provided. It should be noted that, the heater and its control circuit, although having a simplified construction, are provided in the first embodiment shown in FIG. 1, although not shown in the drawing for the sake of simplicity. In this embodiment in FIG. 8, the temperature compensation is based on a predetermined relationship between the temperature of the sensor with respect to the impedance of the sensor. A means is provided for detecting the impedance of the sensor, and comprises an alternate voltage source 371 for adding to the alternate electric signal having a voltage $V_A$ to the electric voltage $V_E$ of the electric voltage source 356a, at a peak-to-peak frequency in a range of between 500 Hz to 100 kHz, and a peak-to-peak amplitude of 0.1 volt. Furthermore, the output of the operating amplifier 350 is connected to the temperature compensation circuit 354, and comprises a detecting circuit 374, an integrating circuit 376, an operating circuit 378, and a transistor 380. The detecting circuit 374 and the integrating circuit 376 obtain the voltage signal VI corresponding to the impedance of the sensor. The operating amplifier 378 is provided with a first inverted input connected to the output of the integrating circuit 376 and a second non-inverted input connected to a voltage generating unit 380, to obtain a reference voltage VIO corresponding to a predetermined value of the impedance of the sensor to be controlled. When the voltage $V_I$ indicating the actual impedance of the sensor is lower than the reference voltage $V_{IO}$, the comparator 378 outputs a high level signal to make the transistor 380 ON, whereby the heater 370 is energized and the temperature of the sensor increased, to increase the impedance of the sensor 300. Conversely, when the voltage VI indicating the actual impedance of the sensor is higher than the reference voltage $V_{IO}$, the comparator 378 outputs a low level signal to make the transistor 380 OFF, whereby the heater 370 is deenergized and the temperature of the sensor lowered, to reduce the impedance of the sensor 300. During this control operation, the temperature of the sensor 300, which corresponds to the impedance thereof, is controlled to a predetermined value.

Figure 10:
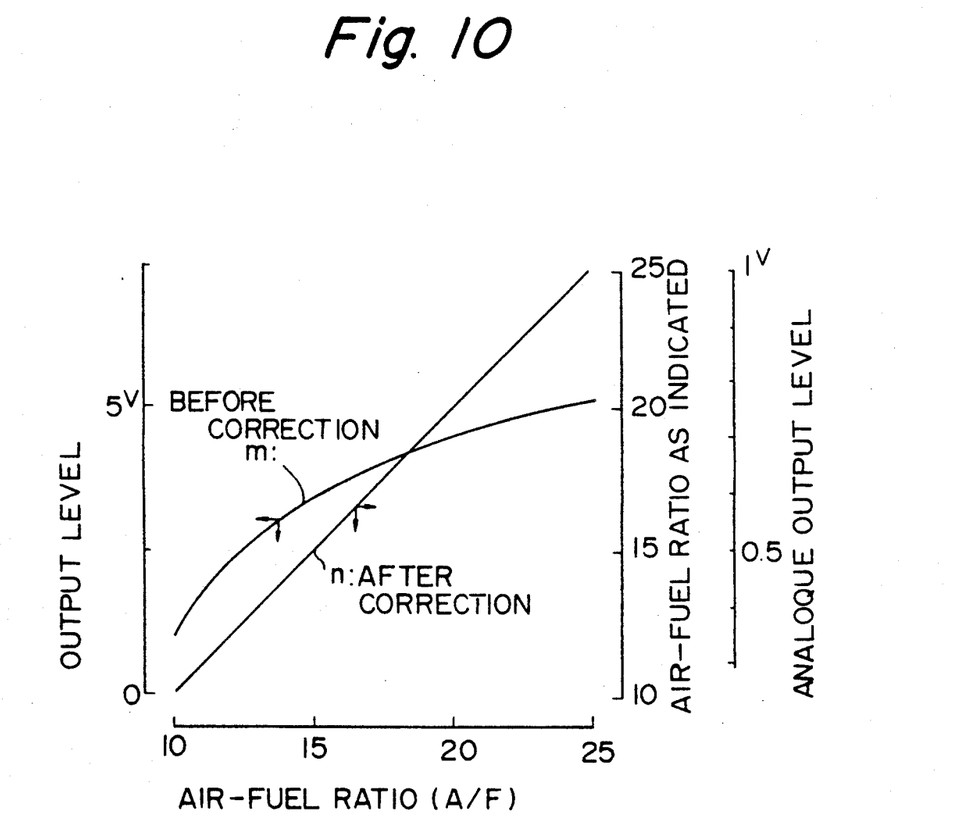

The low pass filter unit 352 eliminates the alternate current component in the signal from the operating amplifier 350, whereby a signal corresponding only to the density of the oxygen can be obtained. In this embodiment, the filter unit 352 is a double filter having a first resistor 382 having a value $R_{10}$, a second resistor 384 having a value $R_{11}$, a first capacitor 386 having a value $C_{10}$, a second capacitor 388 having a value $C_{11}$, and a operating amplifier 390. The capacitor 386 is connected to the non-inverted input of the operating amplifier 390, which is connected to the output of the operating amplifier 390. The capacitors 386 and 388 form a double filter by which the high frequency component is sharply cut, whereby the precision of the detection of the oxygen density is greatly increased. Instead of the above double filter, a simplified low pass filter comprising only a combination of a capacitor and a resistor can be employed. It should be noted that, as will be seen from FIG. 10, a predetermined constant relationship can be obtained between the output from the low pass filter and the air-fuel ratio.

The input end of the feed back resistor 362 is connected to the output of the filter unit 352. This prevents oscillation of the feed back circuit. Namely, the filter unit 352 eliminates an alternate current component from the output of the operating amplifier 390, and therefore, only a direct current component is fed back to the operating amplifier 350 at the positive input 350-2 thereof. If the feed back resistor $R_2$ connected to the positive input 350-2 operating amplifier is connected from the output of the operating amplifier 350 as shown by a dotted line in FIG. 8, an alternate current component is subjected to a positive feed back operation, whereby oscillation of the feed back system is easily begun. This is because (1) the alternate current from the output of the operating amplifier is added to the alternate current at the input 350-2 of the operating amplifier, and (2) this is a positive feed back which, per se, easily generates oscillation. Accordingly, the feed back gain at the high frequency zone becomes extremely high, causing the feed back system to be readily oscillated under a low impedance state after the sensor is activated. In this embodiment, the resistor 362 feeds back only the direct current component from the filter unit 352, and therefore, this oscillation is prevented.

The second embodiment wherein the sensor is used for detection of the air-fuel ratio includes a construction for controlling the air-fuel ratio in an internal combustion engine. Namely, the output of the low pass filter 352 is connected to an input port 353-1 of a microcomputer unit 353 via an analogue-to-digital converter 400. The microcomputer is provided with software, the details of which will not be explained here, which changes the output characteristic as shown by the curved line m in FIG. 10, to a straight line n. The corrected output indicating the detected air-fuel ratio is output from a port 353-2 via an amplifier 402. This corrected output signal is also supplied to a bar indicating circuit 404 and air fuel ratio indicating circuit 406. The port is further connected to a correction switch for correcting a detected air-fuel ratio at predetermined values of the air-fuel ratio, for example, 13.0, 14.6, and 16.0.

Although the present invention is described with reference to embodiments, many modifications and changes can be made by those skilled in this art without departing from the scope and spirit of the present invention.

What is claimed is:

1. An oxygen sensor for detecting oxygen density of an oxygen-containing gas in a region of pulsating pressure, said oxygen sensor comprising:
 a body formed of a solid electrolyte material that is capable of conducting oxygen ions;
 a wall enclosing a portion of the surface of the solid electrolyte body, the wall and the solid electrolyte body forming a hollow structure, the interior of which forms a diffusion chamber; and
 a plurality of electrodes mounted on the structure, the electrodes being adapted to be connected to a voltage source to provide a sensor cell and a pumping cell, wherein
 the structure, when placed in said region of pulsating pressure, is permeable to gas molecules only through at least one pin-hole opening formed in the structure and through a porous portion of the structure not including the pin-hole opening,
 the total flow area of the at least one pin-hole opening is selected to be small enough to control the rate of diffusion of oxygen molecules from the region of pulsating pressure into the diffusion chamber, and the flow area of each pin-hole opening is selected to be large enough to control the diffusion rate primarily by causing multiple collisions between the gas molecules passing through the pin-hole rather than primarily by multiple collisions between the gas molecules and the inner surface of the pin-hole opening, and
 the size of each pore in the porous portion is much smaller than the size of the pin-hole and the total pore area of all the pores in the porous portion is substantially smaller than the flow area of the pin-hole opening but is sufficient to permit pulsative changes in the pulsating pressure region to be transmitted to the diffusion chamber.

2. An oxygen sensor according to claim 1 wherein the porous portion of the structure comprises a plate member formed of a porous material having a predetermined air permeability per unit area.

3. An oxygen sensor according to claim 2 wherein the pin-hole opening is formed in the porous plate member.

4. An oxygen sensor according to claim 2 wherein the total pore area of all the pores in the porous plate member is on the order of 0.01% of the total flow area of the at least one pin-hole opening.

5. An oxygen sensor according to claim 4 wherein the diameter of each pin-hole opening is between about 0.1 mm and about 0.8 mm.

6. An oxygen sensor according to claim 1 wherein said plurality of electrodes comprises two pairs of electrodes, one of the pairs of electrodes serving as the sensor cell and the other of the pairs serving as the pumping cell.

7. An oxygen sensor according to claim 6 wherein both pairs of the electrodes are mounted on the solid electrolyte body.

8. An oxygen sensor according to claim 6 wherein the one pair of electrodes is mounted on the solid electrolyte body and the other pair of electrodes is mounted on the wall.

9. An oxygen sensor according to claim 1 wherein said plurality of electrodes comprises a single pair of electrodes mounted on the solid electrolyte body and serving as both the sensor cell and the pumping cell.

* * * * *